US009026191B2

(12) United States Patent
Assmann et al.

(10) Patent No.: US 9,026,191 B2
(45) Date of Patent: May 5, 2015

(54) METHOD AND DEVICE FOR AUTOMATIC DETERMINATION OF A FLOW OF A BODILY FLUID WITHIN VESSELS OF AN ORGANISM

(75) Inventors: Stefan Assmann, Erlangen (DE); Okan Ekinci, Uttenreuth (DE)

(73) Assignee: Siemens Aktiengesellschaft, Munich (DE)

(*) Notice: Subject to any disclaimer, the term of this patent is extended or adjusted under 35 U.S.C. 154(b) by 1948 days.

(21) Appl. No.: 12/027,335

(22) Filed: Feb. 7, 2008

(65) Prior Publication Data

US 2008/0188737 A1    Aug. 7, 2008

(30) Foreign Application Priority Data

Feb. 7, 2007  (DE) .................... 10 2007 006 142

(51) Int. Cl.
| | |
|---|---|
| *A61B 5/05* | (2006.01) |
| *A61B 5/055* | (2006.01) |
| *A61B 5/02* | (2006.01) |
| *A61B 5/026* | (2006.01) |
| *G06T 5/10* | (2006.01) |
| *G01R 33/563* | (2006.01) |
| *G01R 33/56* | (2006.01) |
| *A61B 6/00* | (2006.01) |

(52) U.S. Cl.
CPC . *A61B 5/055* (2013.01); *G06T 5/10* (2013.01); *G01R 33/563* (2013.01); *G01R 33/56* (2013.01); *A61B 6/5247* (2013.01); *A61B 5/02014* (2013.01); *A61B 5/0263* (2013.01)

(58) Field of Classification Search
None
See application file for complete search history.

(56) References Cited

U.S. PATENT DOCUMENTS

| | | | | |
|---|---|---|---|---|
| 4,718,424 A | * | 1/1988 | Nishimura | 600/419 |
| 4,777,956 A | * | 10/1988 | Macovski | 600/419 |
| 4,849,697 A | * | 7/1989 | Cline et al. | 324/306 |
| 4,947,120 A | * | 8/1990 | Frank | 324/309 |
| 4,993,414 A | * | 2/1991 | Macovski et al. | 600/419 |
| 5,419,325 A | * | 5/1995 | Dumoulin et al. | 600/410 |
| 5,553,619 A | * | 9/1996 | Prince | 600/420 |
| 5,579,767 A | * | 12/1996 | Prince | 600/420 |
| 5,590,654 A | * | 1/1997 | Prince | 600/420 |
| 5,603,319 A | * | 2/1997 | Kuhara et al. | 600/410 |
| 5,647,360 A | * | 7/1997 | Bani-Hashemi et al. | 600/425 |
| 5,671,742 A | * | 9/1997 | Dumoulin et al. | 324/318 |
| 5,746,208 A | * | 5/1998 | Prince | 600/420 |
| 5,762,065 A | * | 6/1998 | Prince | 600/420 |
| 5,792,056 A | * | 8/1998 | Prince | 600/420 |
| 5,799,649 A | * | 9/1998 | Prince | 600/420 |
| 5,827,187 A | * | 10/1998 | Wang et al. | 600/419 |
| 5,869,964 A | * | 2/1999 | Kuhara et al. | 324/309 |
| 5,897,496 A | * | 4/1999 | Watanabe | 600/413 |
| 5,924,987 A | * | 7/1999 | Meaney et al. | 600/420 |
| 6,233,475 B1 | * | 5/2001 | Kim et al. | 600/420 |
| 6,240,311 B1 | * | 5/2001 | Prince | 600/420 |
| 6,311,085 B1 | * | 10/2001 | Meaney et al. | 600/420 |
| 6,438,404 B1 | * | 8/2002 | Van Den Brink et al. | 600/419 |
| 6,463,318 B2 | * | 10/2002 | Prince | 600/420 |

(Continued)

*Primary Examiner* — Nicholas Evoy
(74) *Attorney, Agent, or Firm* — Schiff Hardin LLP

(57) ABSTRACT

In a method and device for automatic determination of a flow of a bodily fluid within vessels of an organism by a magnetic resonance, a magnetic resonance angiography to procedure is implemented generate magnetic resonance angiography images, a of magnetic resonance flow measurement is implemented to generate magnetic resonance flow images, and the magnetic resonance angiography images are applied to the magnetic resonance flow images as a mask to produce a resulting image depicting vessels with flow therein.

20 Claims, 2 Drawing Sheets

(56) References Cited

U.S. PATENT DOCUMENTS

| | | | |
|---|---|---|---|
| 6,552,542 B1* | 4/2003 | Overall | 324/309 |
| 6,556,856 B1* | 4/2003 | Mistretta et al. | 600/420 |
| 6,564,085 B2* | 5/2003 | Meaney et al. | 600/415 |
| 6,597,938 B2* | 7/2003 | Liu | 600/420 |
| 6,618,609 B2* | 9/2003 | Liu et al. | 600/419 |
| 6,647,134 B1* | 11/2003 | McGee et al. | 382/128 |
| 6,662,038 B2* | 12/2003 | Prince | 600/420 |
| 6,741,881 B2* | 5/2004 | Prince | 600/420 |
| 6,754,521 B2* | 6/2004 | Prince | 600/420 |
| 6,842,638 B1* | 1/2005 | Suri et al. | 600/425 |
| 6,879,853 B2* | 4/2005 | Meaney et al. | 600/420 |
| 6,889,072 B2* | 5/2005 | Prince | 600/420 |
| 7,020,314 B1* | 3/2006 | Suri et al. | 382/130 |
| 7,064,545 B2* | 6/2006 | Zaharchuk et al. | 324/307 |
| 7,110,806 B2* | 9/2006 | Prince | 600/420 |
| 7,145,334 B2* | 12/2006 | Assmann et al. | 324/306 |
| 7,336,072 B2* | 2/2008 | Assmann et al. | 324/306 |
| 7,583,992 B2* | 9/2009 | Mistretta et al. | 600/420 |
| 8,165,371 B2* | 4/2012 | Bi et al. | 382/128 |
| 8,233,685 B2* | 7/2012 | Chang et al. | 382/128 |
| 8,275,201 B2* | 9/2012 | Rangwala et al. | 382/173 |
| 8,334,691 B2* | 12/2012 | Lee et al. | 324/306 |
| 8,340,744 B2* | 12/2012 | Bredno et al. | 600/431 |
| 8,374,675 B2* | 2/2013 | Bi et al. | 600/413 |
| 8,428,317 B2* | 4/2013 | Kimia et al. | 382/128 |
| 8,503,741 B2* | 8/2013 | Redel | 382/128 |
| 8,571,288 B2* | 10/2013 | Sugiura | 382/131 |
| 8,571,631 B2* | 10/2013 | Deimling | 600/410 |
| 8,654,119 B2* | 2/2014 | Mistretta et al. | 345/419 |
| 8,706,191 B2* | 4/2014 | Machida | 600/420 |
| 8,811,692 B2* | 8/2014 | Prokoski | 382/128 |
| 8,830,234 B2* | 9/2014 | Mistretta et al. | 345/419 |
| 8,862,202 B2* | 10/2014 | Alexander et al. | 600/410 |
| 2002/0068865 A1* | 6/2002 | Meaney et al. | 600/415 |
| 2002/0177770 A1* | 11/2002 | Lang et al. | 600/410 |
| 2003/0135111 A1* | 7/2003 | Meaney et al. | 600/422 |
| 2004/0162482 A1* | 8/2004 | Assmann et al. | 600/419 |
| 2004/0167394 A1* | 8/2004 | Assmann | 600/419 |
| 2005/0119557 A1* | 6/2005 | Meaney et al. | 600/410 |
| 2005/0156593 A1* | 7/2005 | Assmann et al. | 324/306 |
| 2005/0259854 A1* | 11/2005 | Arimura et al. | 382/130 |
| 2006/0173279 A1* | 8/2006 | Assmann et al. | 600/410 |
| 2006/0241389 A1* | 10/2006 | Assmann et al. | 600/419 |
| 2007/0014452 A1* | 1/2007 | Suresh et al. | 382/128 |
| 2007/0015995 A1* | 1/2007 | Lang et al. | 600/407 |
| 2007/0031019 A1* | 2/2007 | Lesage et al. | 382/131 |
| 2007/0041625 A1* | 2/2007 | Camus et al. | 382/130 |
| 2007/0191704 A1* | 8/2007 | DeCharms | 600/411 |
| 2010/0022869 A1* | 1/2010 | Kimura | 600/419 |

* cited by examiner

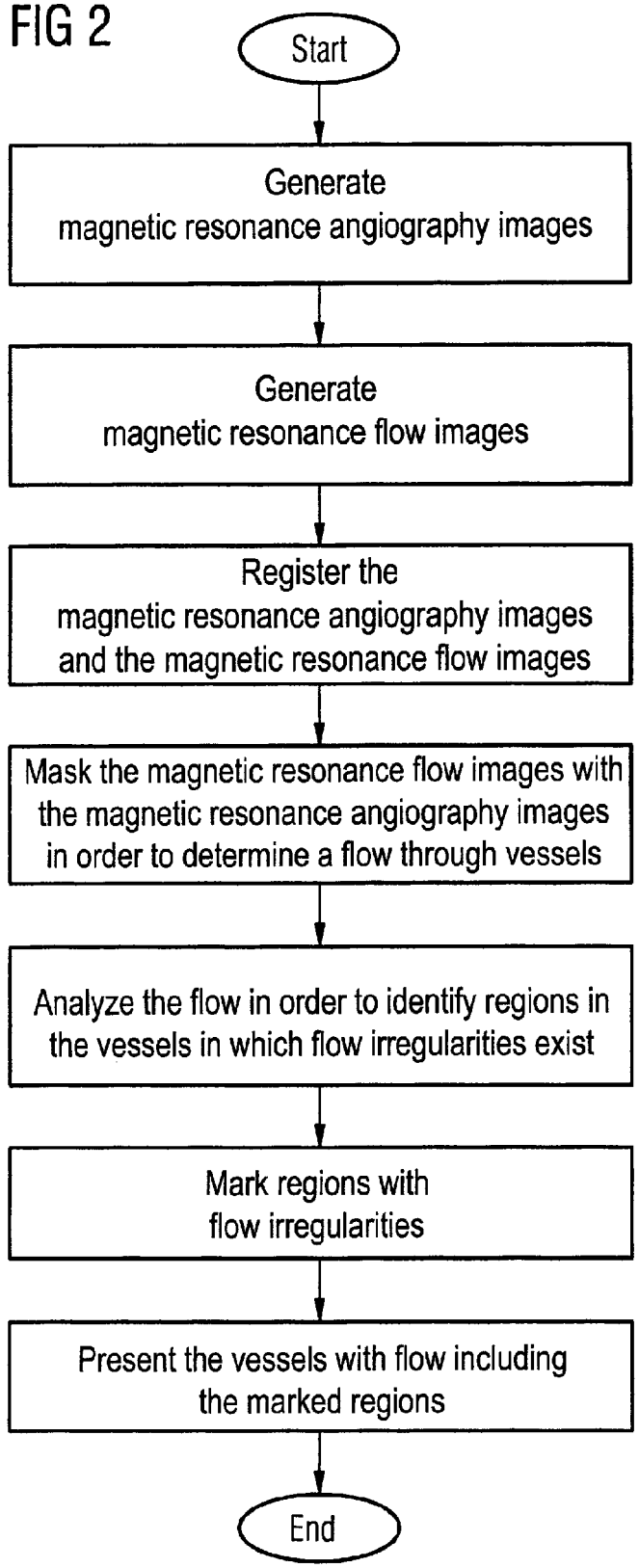

METHOD AND DEVICE FOR AUTOMATIC DETERMINATION OF A FLOW OF A BODILY FLUID WITHIN VESSELS OF AN ORGANISM

BACKGROUND OF THE INVENTION

1. Field of the Invention

The present invention concerns a method for automatic determination of a flow of a bodily fluid within vessels of an organism (in particular a person) by means of magnetic resonance and a correspondingly designed device, particularly for allowing stenoses and aneurysms to be localized and depicted through an analysis of the flow.

2. Description of the Prior Art

Magnetic resonance systems are increasingly used for image-based examination of patients since they enable a relatively stress-free examination of the patient as well as an appraisal of many different body regions of the patient. The manner of operation of such magnetic resonance systems is well known.

Magnetic resonance angiography and magnetic resonance flow measurement can be undertaken with a magnetic resonance system. In magnetic resonance angiography, lumens (in particular blood vessels) within an organism are localized by magnetic resonance tomography and one depicted in images for a physician to interpret. In magnetic resonance flow measurement, moving or flowing elements within the organism are determined and depicted in images for a physician to interpret. Both magnetic resonance angiography and magnetic resonance flow measurement (two-dimensional as well as three-dimensional) are well known to those skilled in the art, so they need not be explained in further detail herein.

Magnetic resonance angiography has conventionally been used, for example, to assist a physician searching for lesions (for example stenoses and aneurysms) by using the corresponding magnetic resonance angiography images. Moreover, with the magnetic resonance flow measurement the physician can check whether the lesions detected with the magnetic resonance angiography are hemodynamically relevant.

In conventional investigation of this type, the physician must manually evaluate magnetic resonance angiography images and magnetic resonance flow images separately from one another in order to identify lesions (such as, for example, stenoses or aneurysms) in a patient.

SUMMARY OF THE INVENTION

An object of the present invention is to provide a method and a device with which lesions (such as, for example, stenoses or aneurysms) in an organism can be identified more simply than is presently possible.

According to the invention, this object is achieved by a method for automatic determination of a flow of a bodily fluid within vessels of an organism by magnetic resonance that includes the steps of generating of magnetic resonance angiography images of an examination subject in a magnetic resonance angiography procedure, generating magnetic resonance flow images by magnetic resonance flow measurements (two-dimensional or three-dimensional), and masking the magnetic resonance flow images through the magnetic resonance angiography images, such that after the masking, vessels with corresponding flow information are identified in the organism.

The superimposition of the magnetic resonance angiography images and the magnetic resonance flow images in the inventive method results in the vessels with a flow being able to determined or identified. Essential information from the magnetic resonance angiography images and the magnetic resonance flow images in combination thus is presented to a physician. For example, the physician can thereby determine stenoses and/or aneurysms in the vessels with less effort than is possible with conventional methods. It should be noted that it is not significant in the inventive method whether the magnetic resonance angiography images are generated before the magnetic resonance flow images or vice versa.

Conventional magnetic resonance images that depict flow information and are used for flow measurement, show information of the entire acquired body region, which includes tissue and vessels at rest. For the physician who analyzes the flow images for diagnosis, it is difficult to optically (mentally) filter out the flow information from the flow images. By the use of magnetic resonance angiography images as a mask, the regions in the flow images that correspond to vessels can be automatically identified according to the invention. Moreover, the regions in the flow image that contain no vessel information can be automatically masked out by means of the angiography information.

Through registration and the subsequent superimposition or masking of the magnetic resonance flow images with the magnetic resonance angiography images, in particular only the flow of bodily fluids that flow through the vessels of the organism is determined. In other words, any flow information outside of the vessels is removed so that only the flow through the vessels can be presented to the physician. This offers the advantage that, in the analysis of the flow, the physician is not distracted by flow movements outside of the vessels.

As used herein, "registration" means that the magnetic resonance flow images are fused or synchronized with the magnetic resonance angiography images so they are aligned exactly relative to one another in the subsequent superimposition such that, given a superimposition of a magnetic resonance flow image with an associated magnetic resonance angiography image, overlapping regions of the two images of the same body regions correspond.

In the inventive embodiment the flow in the vessels is analyzed automatically in order to identify regions within the vessels in which the flow exhibits irregularities. For example, an analysis can identify areas within the vessels in which a speed gradient (a change of a flow speed dependent on the location) is greater in terms of magnitude than a predetermined threshold. Moreover, the analysis can identify regions within the vessels in which a non-laminar flow is present or, respectively, in which the flow exhibits turbulences.

Since blood speed is average before and after a stenosis (constriction) but is high within the stenosis (thus higher than in the flow direction before or after the stenosis), the stenosis can be identified by an analysis of the speed gradients. By contrast, given an aneurysm the flow speed before and after the aneurysm is average and is low within the aneurysm (lower than in the flow direction before or after the aneurysm), such that an aneurysm also can be identified by analysis of the speed gradients. A further indicator of a lesion is the degree of turbulence within the flow, wherein it can lead to flow diminution or eddies in the magnetic resonance flow images in areas in which corresponding turbulences occur, such that turbulences and therewith a lesion can be extrapolated using these diminutions or eddies or, respectively, inhomogeneities.

The regions in which an irregularity of the flow has been determined can be presented in an advantageous manner so that they are differentiable by a physician from other regions in which the current flows regularly or homogeneously. For example, for this purpose the magnetic resonance angiography images can be presented as a shaded surface display or by means of the volume rendering technique, wherein areas of a suspected lesion are characterized by a color overlay. The color intensity of the color overlay can be used in order to represent the risk potential of the corresponding lesion with differing color intensity. For example, the color intensity of a high-grade stenosis could be greater than that of a lower-grade stenosis. Moreover, it is possible to characterize the type of the lesion by means of a corresponding color tone, such that stenoses are characterized with a different color tone than aneurysms, for example.

Moreover, it is possible to present the magnetic resonance angiography images by means of two-dimensional or three-dimensional maximum intensity projection, wherein regions of a possible lesion are marked in color.

According to an inventive embodiment, the flow within the vessels can be simulated by moving particles, so the magnetic resonance angiography images can be presented as semi-transparent. The particles thereby move corresponding to the speeds and directions of the flow measurement. The density of the particles at one point can also be adjusted or simulated such that the density is increased as the current speed of the flow, which has been previously determined or calculated at this point, increases. The density and the color of the particles thus vary correspondingly given passage through a lesion (for example a stenosis) and thus, as an animation, serve as an optical aid for analysis of the corresponding lesion by a physician.

The inventive method can ensue either "online", (meaning simultaneously with the generation of the corresponding magnetic resonance angiography images and magnetic resonance flow images directly after an acquisition of a last data set), or "offline" (meaning the superimposition of the magnetic resonance flow images by the magnetic resonance angiography images ensues subsequently on magnetic resonance angiography images and magnetic resonance flow images already determined previously), for example by operating personnel (for example a physician) activating the appropriate (desired) image processing.

Two groups of magnetic resonance angiography images and magnetic resonance flow images can also be evaluated to determine lesions. For this purpose, a group of images is generated before an administration of a medicine (for example a vasodilator to expand the vessels or a blood thinner) while the other group of images is generated after the administration of the medicine. For medicines (such as, for example, a vasodilator) which act virtually immediately, according to the invention only the magnetic resonance flow images need be generated after the administration of the medicine. Since in this case the patient remains in the magnetic resonance system, the magnetic resonance angiography images generated before the administration of the medicine (which magnetic resonance angiography images can be stored in a memory of the magnetic resonance system) can also be used as the magnetic resonance flow images generated after the medicine administration, as discussed below. In other words, generation of the magnetic resonance angiography images after the administration of the medicine is foregone, so the inventive method is advantageously accelerated since the generation of the magnetic resonance angiography images normally takes multiple minutes.

In this embodiment, registration of the magnetic resonance angiography images with the generated magnetic resonance flow images and masking of the magnetic resonance angiography images with the magnetic resonance flow images generated after the administration of the medicine are implemented after the administration of the medicine. Differences with regard to the flow before and after the administration of the medicine are thereby determined by comparing the results of the flow measurement with regard to the magnetic resonance flow images generated before the administration with the results of the flow measurement with regard to the magnetic resonance flow images generated after the administration, and regions in which these results are clearly different are depicted by a corresponding color superimposition, for example.

For example, regions within the vessels can be determined in which a difference (with regard to the speed measured by the flow measurement) between the results before the administration and the results after the administration lies above a predetermined threshold. Regions in which a difference that is representative of turbulence in the flow between the results before the administration and the results after the administration lies above a further predetermined threshold can be determined in a similar manner.

In cause of administration of a blood thinner, which normally only becomes active after many hours, stenoses (for example), which were formed due coagulation of blood components before the administration of the blood thinner, may have been eliminated by the blood thinning, such that a corresponding stenosis is no longer detected given an analysis of the results after the administration of the blood thinner. By presenting a region to the physician that corresponds to the location of a stenosis due to blood coagulation before administration of the blood thinner, the inventive comparison between the results before and after the administration allows the physician to differentiate between stenoses which occur due to a blood coagulation and stenoses that arise due to some other cause.

The above object is achieved in accordance with the present invention by a device for automatic identification of a flow of a bodily fluid within vessels of an organism. The device has a unit for generation of magnetic resonance angiography images and a further unit for generation of magnetic resonance flow images. The device is fashioned to mask the magnetic resonance flow images with the magnetic resonance angiography images such that the vessels with flow are determined.

The advantages of the inventive device correspond to the advantages of the inventive method as described above, so these advantages need not be repeated.

The present invention is advantageously suited for evaluation of results that have been generated with a magnetic resonance system, but the present invention is naturally not limited to this known application field but rather can be used anywhere where images of any fluid conducting conduit system exist and images or results of elements moving through this system exist as well, such that a superimposition of these images of the fluid conducting conduit system can be analyzed, for example with regard to bottlenecks.

BRIEF DESCRIPTION OF THE DRAWINGS

FIG. 2 is a flowchart of an inventive method.

DESCRIPTION OF THE PREFERRED EMBODIMENTS

Figure 1:
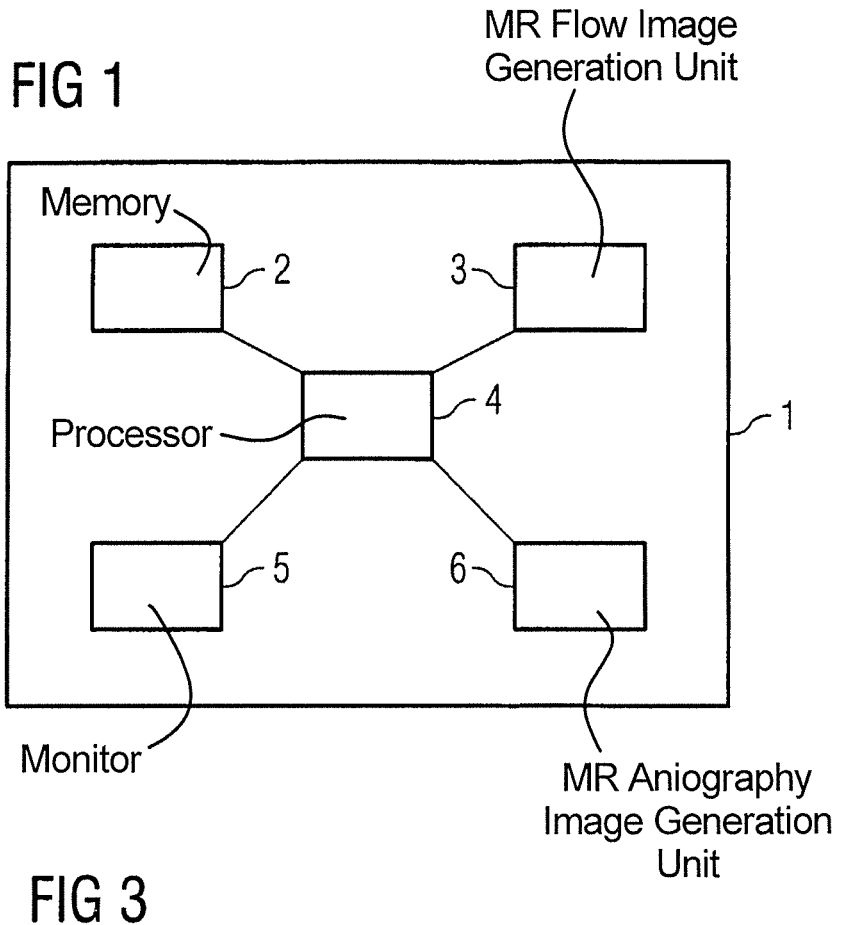
FIG. 1 schematically illustrates an embodiment of an inventive device.

An inventive device 1 for automatic determination and presentation of flow irregularities of a bodily fluid within vessels 11 of an organism is shown in FIG. 1. The device 1 includes a unit 3 for generation of magnetic resonance flow images, a unit 6 for generation of magnetic resonance angiography images, a processor 4 and a monitor 5 in order to be able to present results determined from the generated images. The device 1 also includes a memory 2 in order to be able to store the magnetic resonance flow images and the magnetic resonance angiography images for specific inventive methods.

A program workflow diagram of an inventive method is shown in FIG. 2. In a first step of the method, magnetic resonance angiography images of a patient are generated in a magnetic resonance system. In a second step magnetic resonance flow images of the same body regions from which the magnetic resonance angiography images were generated in the first step are generated from the same patient. In a further step of the inventive method the magnetic resonance angiography images and the magnetic resonance flow images are subsequently registered, meaning that the same body regions of corresponding magnetic resonance angiography images and magnetic resonance flow images are respectively aligned on one another such that they overlap one another virtually exactly with regard to the corresponding body regions. After this registration step the magnetic resonance flow images are masked with the magnetic resonance angiography images such that the images resulting from this shown only vessels, wherein information about the flow in these vessels exists within the vessels due to the magnetic resonance flow images. In a further step of the inventive method the flow in the vessels can now be analyzed in order to identify regions in which flow irregularities exist in the vessels. Regions within the vessels in which lesions (for example stenoses or aneurysms) exist can then be determined from these flow irregularities in this step. The identified lesions are then marked (for example by color) in a further step and presented (for example to a treating physician) on a display unit in the last step of the inventive method.

It is noted that the two steps "generation of magnetic resonance angiography images" and "generation of magnetic resonance flow images" can also be executed in a reversed order relative to the order shown in FIG. 2.

Figure 3:
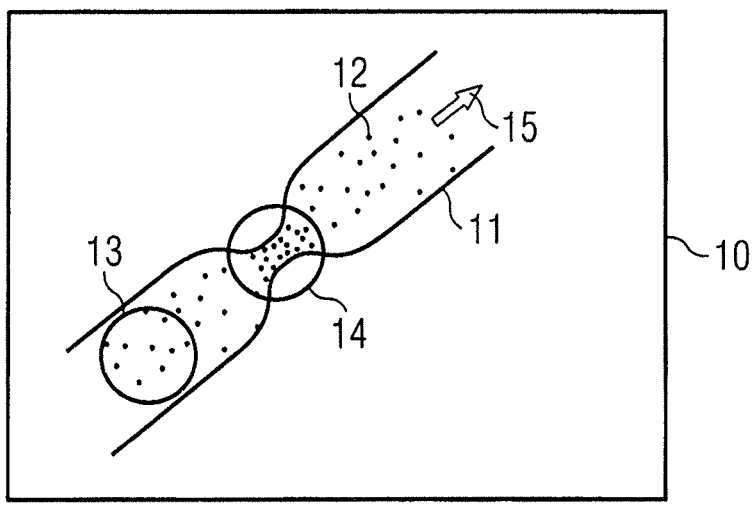
FIG. 3 is a depiction of a pictorial result of a preferred exemplary embodiment.

A preferred exemplary embodiment for presentation of flow irregularities is presented in FIG. 3. A blood vessel 11 with a stenosis 14 is shown on a monitor image 10. This stenosis is identified in that the inventive method analyzes the flow within the blood vessel 11 and determined a region 14 with increased speed gradients. This means that, given an analysis of the speed of individual blood particles, 12, the inventive method detects that in the region 14 there are different speeds for the individual particles 12 dependent on the location. The speed of the blood particles 12 is highest at a point in which the blood vessel 11 is most constricted while the speed of the blood particles 12 decreases both in the flow direction 15 and counter to the flow direction from this point.

The flow speed of the particles 12 is already average in a region identified with a reference character 13, wherein a laminar flow occurs in the region 13. In addition to the increased speed gradients the region 14 is also characterized in that here turbulences occur in the current, which is also inventively detected and contributes to the inventive method identifying a stenosis at this point.

The flow through the blood vessel 11 is inventively presented on the monitor image 10 in that individual particles 12 are shown within the vessel 11. These particles 12 thereby exhibit a flow speed of the current at the corresponding point or, respectively, the inventive method simulates the particles 12 with the corresponding flow speed so that, in the case presented in FIG. 3, the particles 12 move faster in the region 14 (due to the narrow point or, respectively, stenosis located there) than in the region 13. Moreover, the number of the particles per volume unit is higher in the region 14 (due to the constriction there) than in the region 13 (the inventive method simulates more particles 12 in the region 14 than in the region 13), wherein it is additionally depicted that the speed in this region 14 is increased in comparison to the speed in the region 13. The region 14 is marked in color such that it differs from other regions (such as, for example, the region 13) such that it is indicated to an observer of the monitor image 10 that the inventive method has detected or identified a suspected lesion in the region 14.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for automatically determining a flow of a bodily fluid within vessels of an organism by magnetic resonance, comprising the steps of:

operating a magnetic resonance apparatus with a subject situated therein to implement a magnetic resonance angiography procedure to obtain a magnetic resonance angiography image of the subject in which vessels are depicted;

operating said or a different magnetic resonance apparatus with the subject situated therein to implement a magnetic resonance flow measurement to generate a magnetic resonance flow image of the subject in which a flow of a bodily fluid in the subject is depicted;

providing the magnetic angiography image and the magnetic resonance flow image to a computer and, in the computer, automatically executing a computerized algorithm in which the magnetic resonance angiography image is applied to the magnetic resonance flow image as a mask to produce a further image in which said vessels in the subject are depicted with said flow of the bodily fluid depicted in the vessels; and in said computerized algorithm, also automatically electronically analyzing, in said computer, said flow of said bodily fluid depicted in said vessels in said further image, by determining a speed gradient of the flow in said vessels and automatically identifying, from said speed gradient, at least one region in said vessels, selected from the group consisting of a region in said vessels wherein said speed gradient has a magnitude that is larger than a predetermined threshold, and a region in said vessels having an absence of laminar flow, and displaying said further image with said at least one region having an artificially added visual appearance that differs from the depiction of said flow of said bodily fluid depicted in said further image outside of said at least one region.

2. A method as claimed in claim 1 comprising, in said computerized algorithm in said computer, applying the magnetic resonance angiography image as said mask to show, in said further image, only vessels in said angiography image that have flow of said bodily fluid therein, with flow outside of said vessels not being depicted.

3. A method as claimed in claim 1 comprising depicting said magnetic resonance angiography image in the display of said further image as a shaded surface display or with a volume rendering technique, and superimposing said at least one region in said further image in color, as said artificially added visual appearance, on said magnetic resonance angiography image in said further image.

4. A method as claimed in claim 1 comprising depicting said magnetic resonance angiography image in the display of said further image as a two-dimensional or three-dimensional maximum intensity projection, and superimposing said at least one region in color, as said artificially added visual appearance, on the magnetic resonance angiography image in said further image.

5. A method as claimed in claim 1 comprising:
depicting said at least one region a color, as said artificially added visual appearance, in said further image, said color having a color intensity that is dependent on said speed gradient.

6. A method as claimed in claim 1 comprising depicting said flow in said vessels in said further image with a plurality of simulated particles moving through said vessels in a direction corresponding to said flow, and depicting said particles with a characteristic, selected from the group consisting of particle density and particle speed, that is dependent on said speed gradient.

7. A method as claimed in claim 1 comprising applying said magnetic resonance angiography image to said magnetic resonance flow image as said mask simultaneously with implementation of said magnetic resonance angiography procedure and implementation of said magnetic resonance flow measurement.

8. A method as claimed in claim 1 comprising electronically storing said magnetic resonance angiography image and said magnetic resonance flow images and applying the electronically stored magnetic resonance angiography images to the electronically stored magnetic resonance flow image as said mask at a time subsequent to implementation of said magnetic resonance angiography procedure and implementation of said magnetic resonance flow measurement.

9. A method as claimed in claim 1 comprising:
administering a medicine to the subject that influences said flow in the subject;
implementing said magnetic resonance flow measurement before administering said medicine and after administering said medicine, to produce a pre-administration further image and a post-administration further image, respectively; and
displaying said pre-administration further image and said post-administration further image with said artificially added visual appearance allowing differences in the flow in said at least one region respectively depicted therein to be identified.

10. A method as claimed in claim 1 comprising implementing said magnetic resonance flow measurement as a three-dimensional flow measurement.

11. A device for automatically determining a flow of a bodily fluid within vessels of an organism by magnetic resonance, comprising:
a magnetic resonance angiography unit that obtains a magnetic resonance angiography image, in which vessels are depicted, of a subject;
a magnetic resonance flow measurement unit that generates a magnetic resonance flow image of the subject, in which a flow of a bodily fluid in the subject is depicted;
a processor configured to apply the magnetic resonance angiography image to the magnetic resonance flow image as a mask to produce a further image that depicts said vessels in the subject with said flow of the bodily fluid in the vessels;
a monitor in communication with said processor causes; and
said processor being configured to automatically analyze said flow in said vessels in said further image by determining a speed gradient of the flow in said vessels and automatically identifying, from said speed gradient, at least one region in said vessels, selected from the group consisting of a region in said vessels wherein said speed gradient has a magnitude that is larger than a predetermined threshold, and a region in said vessels having an absence of laminar flow, and to cause said further image to be displayed at said monitor with said at least one region having an artificially added visual appearance that differs from the depiction of said flow of said bodily fluid depicted in said further image outside of said at least one region.

12. A device as claimed in claim 11 wherein said processor is configured to apply the magnetic resonance angiography image to the magnetic resonance flow image as said mask to show, in said further image, only vessels with flow of said bodily fluid therein, with no flow information outside of said vessels.

13. A device as claimed in claim 11 wherein said processor is configured to cause said further image to be displayed at said monitor as a shaded surface display or with a volume rendering technique, and with said at least one region superimposed, in color on said magnetic resonance angiography image in said further image.

14. A device as claimed in claim 11 wherein said processor is configured to cause said magnetic resonance angiography image in said further image to be displayed at said monitor as a two-dimensional or three-dimensional maximum intensity projection, and with said at least one region superimposed in color on the magnetic resonance angiography image in said further image.

15. A device as claimed in claim 11 wherein said processor is configured to cause said at least one region to be displayed at said monitor with a color, as said artificially added visual appearance, in said further image, said color having a color intensity that increases dependent on said speed gradient.

16. A device as claimed in claim 11 wherein said processor is configured to cause said further image to be displayed at said monitor with said flow in said vessels in said further image depicted with a plurality of simulated particles, as said artificially added visual appearance, moving through said vessels in a direction corresponding to said flow, with said particles depicted with a characteristic, selected from the group consisting of particle density and particle speed, that increases dependent on said speed gradient.

17. A device as claimed in claim 11 wherein said processor is configured to apply said magnetic resonance angiography image to said magnetic resonance flow image as said mask simultaneously with implementation of said magnetic resonance angiography procedure and implementation of said magnetic resonance flow measurement.

18. A device as claimed in claim 11 comprising a memory accessible by said processor in which said processor is configured to electronically store said magnetic resonance angiography image and said magnetic resonance flow image, and wherein the processor is configured to apply the electronically stored magnetic resonance angiography image to the electronically stored magnetic resonance flow images as said mask at a time subsequent to implementation of said magnetic resonance angiography procedure and implementation of said magnetic resonance flow measurement.

19. A device as claimed in claim 11 wherein a medicine is administered to the subject that influences said flow in the subject, and wherein said magnetic resonance flow measurement unit implements said magnetic resonance flow measurement before said medicine is administered and after said medicine is administered, to produce a pre-administration further image and a post-administration further image, respectively, and wherein said processor is configured to cause said pre-administration further image and said post-administration further image to be displayed at said monitor with said artificially added visual appearance differences in the flow in said at least one region respectively depicted therein to be identified.

20. A device as claimed in claim 11 wherein said magnetic resonance flow measurement unit implements said magnetic resonance flow measurement as a three-dimensional flow measurement.

\* \* \* \* \*